US00PP21807P2

(12) United States Plant Patent
Utecht

(10) Patent No.: US PP21,807 P2
(45) Date of Patent: Mar. 22, 2011

(54) ***PELARGONIUM* PLANT NAMED 'FIX 137'**

(50) Latin Name: ***Pelargonium peltatum* (L.)**
Varietal Denomination: Fix 137

(75) Inventor: Angelika Utecht, Montabaur (DE)

(73) Assignee: Syngenta Crop Protection AG, Basel (CH)

( * ) Notice: Subject to any disclaimer, the term of this patent is extended or adjusted under 35 U.S.C. 154(b) by 49 days.

(21) Appl. No.: 12/383,421

(22) Filed: Mar. 24, 2009

(51) Int. Cl.
*A01H 5/00* (2006.01)

(52) U.S. Cl. ..... Plt./332

(58) Field of Classification Search ..... Plt./332
See application file for complete search history.

(56) References Cited

U.S. PATENT DOCUMENTS

PP18,383 P2 * 1/2008 Utecht ..... Plt./332

OTHER PUBLICATIONS

Attachment "A" and Attachment "B".*

* cited by examiner

*Primary Examiner*—Susan B McCormick Ewoldt
(74) *Attorney, Agent, or Firm*—S. Matthew Edwards

(57) ABSTRACT

A new *Pelargonium* plant named 'Fix 137,' particularly distinguished by the white flower color, open, single-type flowers, early and rich flowering, glossy, deep green foliage, ivy-shaped with distinct lobes and distinct zonation, fairly vigorous growth, tall, bushy and well-branched, trailing plant habit.

1 Drawing Sheet

Latin name of the genus and species of the plant claimed: *Pelargonium peltatum* (L.).

Varietal denomination: 'Fix 137'.

BACKGROUND OF THE NEW PLANT

The present invention comprises a new ivy *Geranium*, botanically known as *Pelargonium peltatum* and hereinafter referred to by the variety name 'Fix 137'.

'Fix 137' is a product of a planned breeding program. The new cultivar has white, single-type flowers, deep green, glossy foliage with distinct zonation, vigorous growth, trailing plant habit and very good branching characteristics.

'Fix 137' originated from a hybridization made in the summer of 2002 in a controlled breeding program in Hillscheid, Germany. The female parent was a seeding derived by self-pollination of a wild *Pelargonium peltatum* plant, designated as 'i99-2043-8', with white flowers, medium to late flowering, and a more compact plant habit with less vigor.

The male parent of 'Fix 137' was a seeding grown out of a unpatented, seed propagated variety commercially known as 'Tornado' with smaller white flowers, early flowering, strong seed set, foliage with weak zonation, and long and relatively thin, but strong branching.

'Fix 137' was selected as one flowering plant within the progeny of the stated cross in the spring of 2003 in a controlled environment in Galdar, Gran Canaria, Spain.

The first act of asexual reproduction of 'Fix 137' was accomplished when vegetative cuttings were taken from the initial selection in the fall of 2003 in a controlled environment in Galdar, Gran Canaria, Spain.

Horticultural examination of plants grown from cuttings of the plant initiated in February of 2004 in Hillscheid, Germany, and continuing thereafter, has demonstrated that the combination of characteristics as herein disclosed for 'Fix 137' are firmly fixed and are retained through successive generations of asexual reproduction.

'Fix 137' has not been observed under all possible environmental conditions. The phenotype may vary significantly with variations in environment such as temperature, light intensity and day length.

Plant Breeder's Rights for this cultivar were applied for in Germany on Mar. 25, 2008, in the European Union on Oct. 10, 2008, and in Canada on Feb. 11, 2009. 'Fix 137' has not been made publicly available more than one year prior to the filing of this application.

BRIEF DESCRIPTION OF THE DRAWINGS

The accompanying photographic drawing show typical flower and foliage characteristics of 'Fix 137' with colors being as true as possible with an illustration of this type. The photographic drawing in FIG. 1 shows a close-up of the flower and in FIG. 2 shows three six month old plants of the new variety in a hanging basket. The photographs were taken in early August 2007 in Hillscheid, Germany.

DETAILED BOTANICAL DESCRIPTION

Figure 1:
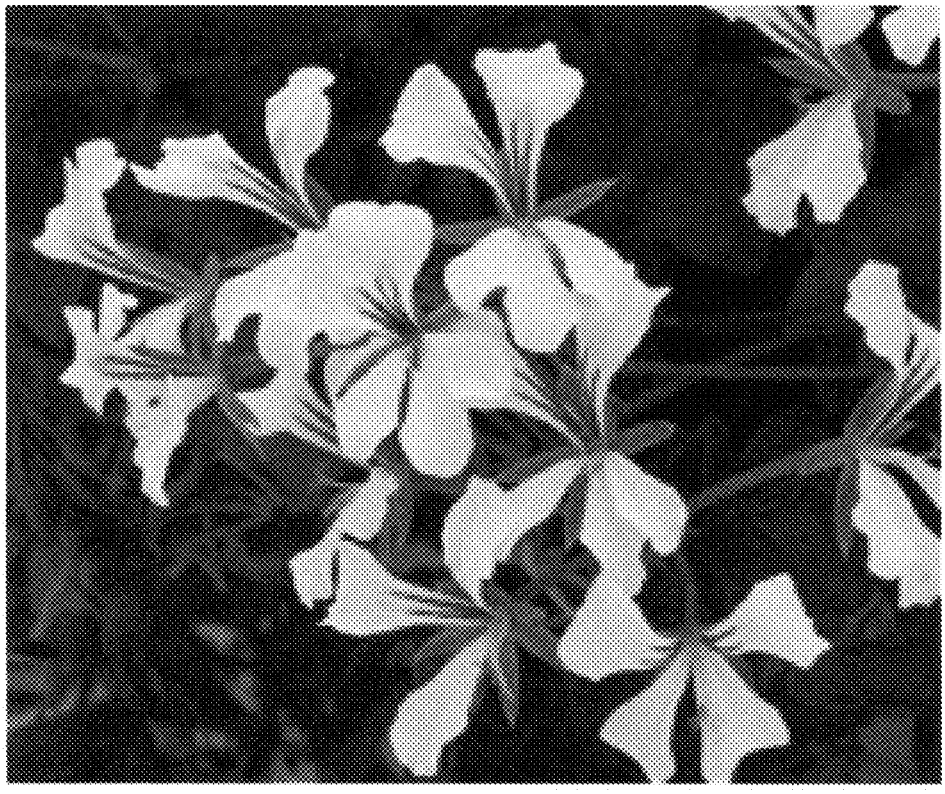
Figure 2:
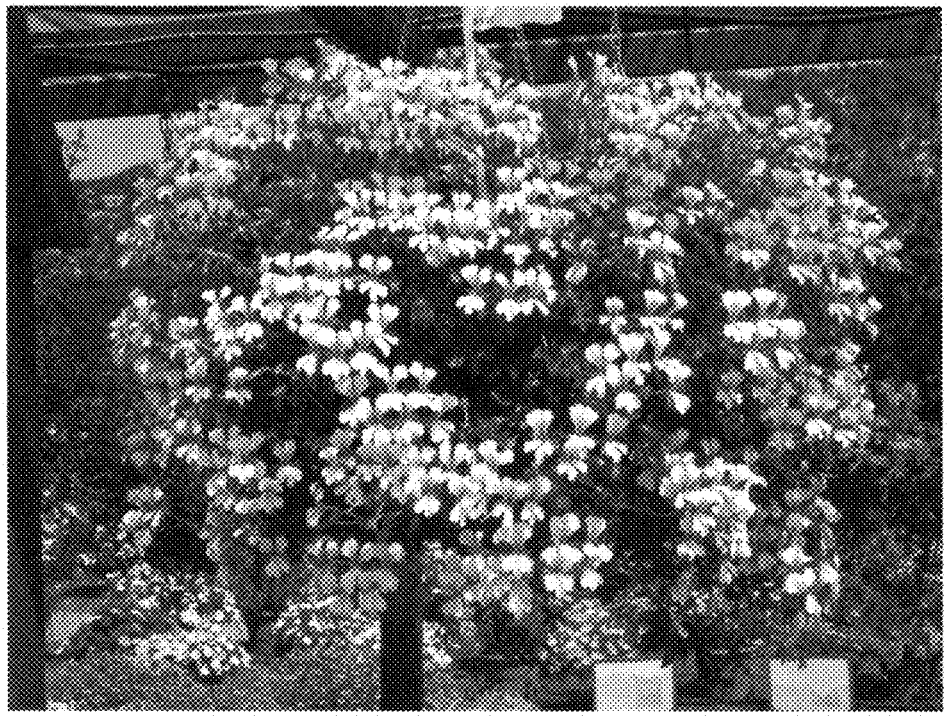

The measurements were taken in Hillscheid, Germany, in mid May 2008 on 13 week old plants that were growing in a greenhouse at a minimum temperature of 14° C. at night and 16° C. in daytime. Culture of these plants had started in early February 2008 when rooted young plants were planted into 12 cm pots and were pinched once.

Color chart used: Royal Horticultural Society Colour Chart (R.H.S.) 2001.

BRIEF SUMMARY OF INVENTION

The following observations, measurements, and comparisons describe plants grown indoors in Hillscheid/Germany and Chatellerault, France. The following traits have been repeatedly observed and are determined to be basic characteristics of the new variety. The combination of these characteristics distinguishes this *Pelargonium* as a new and distinct variety.

1. White, single-type flowers with red-purple stripes.
2. Large inflorescences and large, open flowers.
3. Deep green foliage, relatively small leaves with distinct zonation.
4. Vigorous growth, bushy, relatively tall plant size.
5. Freely branching, trailing plant habit.
6. Early flowering response.

TABLE 1

DIFFERENCES BETWEEN THE NEW VARIETY 'FIX 137' AND SIMILAR VARIETIES

| | 'Fix 137' | 'Fisnow' (U.S. Plant Pat. No. 18,383) |
|---|---|---|
| Flower color | Pure white | White, may show a light pink overtone |
| Pedicel and sepal color | Green | Green at base, mainly purple |
| Leaf zone (from 1 absent to 9 very strong) | Medium to strong | Strong |
| Foliage color | Deep green | Medium green |

In comparison to 'Fisbliz,' U.S. Plant Pat. No. 9,373, 'Fix 137' has differently shaped flowers with narrower petals that do not overlap, thus flowers of 'Fix 137' are closer to flowers of wild *Pelargonium peltatum*, while flowers of 'Fisbliz' appear rounder with nearly no gaps between petals. Additionally, 'Fix 137' starts flowering earlier than 'Fisbliz' and has smaller leaves.

Plant:

*Form, growth and habit.*—Bushy, freely branching, ascending to prostrate, then trailing, suitable especially for hanging baskets and window baskets.

*Plant height.*—14.5 cm.

*Plant diameter.*—40.3 cm.

*Plant size at the end of the summer.*—85-90 cm (6 months old, measured from the base of the main stem to the tips of shoots).

Stem:

*Number of branches.*—16-18.

*Color of stem.*—RHS 143B.

*Length of stem.*—22-36 cm.

*Diameter.*—4-5 mm.

*Length of internodes.*—2.5-4 cm.

*Texture.*—Smooth, nearly glabrous.

Foliage:

*Immature, leaf color, upper surface.*—RHS 137D.

*Lower surface.*—RHS 143B.

*Mature leaf color, upper surface.*—RHS 137A-137B, deep green.

*Lower surface.*—RHS 137D.

*Length.*—8.2 cm.

*Width.*—6.1 cm.

*Shape.*—Ivy-shaped (palmatisect) with rounded lobes.

*Base shape.*—Cordate, open gap between the lowest lobes.

*Apex shape.*—Rounded.

*Margin.*—Entire.

*Texture.*—Leathery, surface appears smooth and somewhat glossy.

*Leaf zone.*—RHS 166A (dark brown), narrow, of medium to strong distinctness.

*Color of veins, upper surface.*—Indistinct, RHS 137D.

*Color of veins, lower surface.*—RHS 144A.

Petiole:

*Color.*—RHS 143A.

*Petiole length.*—4.9 cm.

*Diameter of petiole.*—2-2.5 mm.

*Texture.*—Nearly glabrous.

Inflorescence:

*Start of flowering.*—50% of plants were flowering on May 5, 11 weeks old (10 weeks old in 2007).

*Duration of flowering.*—Continuous flowering throughout the summer.

*Durability of inflorescence on the plant.*—About 12-15 days, petals are self-cleaning ('shattering').

*Number of flowers per inflorescence.*—9.5.

*Number of inflorescences per plant.*—4-7.

*Type of inflorescence.*—An umbel, of irregular, incomplete shape.

*Umbel diameter.*—11.3 cm.

*Umbel depth.*—6.5-7.5 cm.

Peduncle:

*Color.*—RHS 137D, no anthocyanin.

*Length of peduncle.*—14.2 cm.

*Peduncle diameter.*—2.5 mm.

*Texture.*—Smooth, sparse hair.

Pedicel:

*Color.*—RHS 137D.

*Length of pedicel.*—4.1 cm.

*Diameter of pedicel.*—2 mm.

*Texture.*—Nearly glabrous.

Corolla:

*Form.*—Single-type, zygomorphic, open, with the petals not overlapping and with distinct gaps between upper and lower petals.

*Diameter (length) of flower.*—5.1 cm.

*Depth of flowers.*—1.5-1.8 cm.

*Number of petals.*—5.

*Color upper petals, upper surface.*—Whiter than RHS 155D, at the base distinct red-purple veins, RHS 187C.

*Color upper petals, lower surface.*—RHS 155D.

*Length of upper petals.*—3.0-3.3 cm.

*Width of upper petals.*—1.7-1.8 cm.

*Color lower petals, upper surface.*—Whiter than RHS 155D, no markings.

*Color lower petals, lower surface.*—RHS 155D.

*Length of lower petals.*—2.4-2.6 cm.

*Width of lower petals.*—1.5-1.7 cm.

*Petal shape.*—Spatulate (upper petals) and obovate (lower petals).

*Apex shape.*—Truncate or retuse (upper petals); rounded (lower petals).

*Margin.*—Entire, possibly weakly crenulated at the apex.

*Petal texture.*—Smooth, glabrous.

*Number of petaloids.*—None.

Bud (just before opening):

*Color.*—White, RHS 155A.

*Length.*—2.3-2.4 cm.

*Width.*—8-9 mm.

*Shape.*—Elliptic, narrow.

Calyx:

*Number of sepals.*—5.

*Color of sepals.*—Green, RHS 137D, for the outer, visible surface.

*Length of sepals.*—1.0-1.1 cm.

*Width of sepals.*—0.5 cm for the largest sepal, 0.3-0.4 cm for the other ones.

*Sepal shape.*—Lanceolate.

*Apex shape.*—Acute, pointed.

*Margins.*—Entire.

*Texture.*—A few relatively long, soft hairs.

Reproductive organs:

*Pistil.*—One.

*Length.*—1.3 cm.

*Style color.*—RHS 155A, white.

*Style length.*—0.6 cm.

*Stigma color.*—Pink, RHS 68B.

*Number of anthers.*—7.

*Length of anthers.*—3 mm.

*Anther color.*—RHS 187C, purple.

*Length filaments.*—8-12 mm.

*Color of filaments.*—Mainly white, RHS 155D, upper part light pink, RHS 68D.

*Pollen amount.*—Plenty.

*Color of pollen.*—Yellow-orange, RHS 23A.

*Fertility/seed set.*—Moderately, mainly in late summer to fall.

*Fruit.*—Oblong, about 10 mm in length and 6 mm in diameter, total length with rostrum (beak) is 4.5 cm.

*Seed.*—Oblong, 4-5 mm long, 3 mm in diameter, brown.

Disease/pest resistance: Disease resistance or susceptibility has not been observed on this hybrid.

What is claimed is:

1. A new and distinct variety of *Pelargonium* plant named 'Fix 137,' substantially as illustrated and described herein.

* * * * *